(12) United States Patent
Boehm et al.

(10) Patent No.: US 7,468,246 B2
(45) Date of Patent: Dec. 23, 2008

(54) IDENTIFICATION AND USE OF INHIBITORS OF HAIR GROWTH

(75) Inventors: Thomas Boehm, Vorstetten (DE); Thomas Schlake, Gundelfingen (DE)

(73) Assignee: Max-Planck-Gesellschaft zur Forderung der Wissenschaften e.V., Berlin (DE)

( * ) Notice: Subject to any disclaimer, the term of this patent is extended or adjusted under 35 U.S.C. 154(b) by 593 days.

(21) Appl. No.: 10/469,821

(22) PCT Filed: Mar. 6, 2002

(86) PCT No.: PCT/EP02/02470

§ 371 (c)(1),
(2), (4) Date: Apr. 26, 2004

(87) PCT Pub. No.: WO02/070743

PCT Pub. Date: Sep. 12, 2002

(65) Prior Publication Data

US 2004/0180024 A1    Sep. 16, 2004

(30) Foreign Application Priority Data

Mar. 7, 2001    (EP)    ................................ 01105335.2

(51) Int. Cl.
*C12Q 1/68*    (2006.01)
(52) U.S. Cl. ........................ 435/6; 435/320.1; 530/350; 424/70.1
(58) Field of Classification Search ........................ None
See application file for complete search history.

(56) References Cited

FOREIGN PATENT DOCUMENTS

| DE | 19831043 | 1/2000 |
|---|---|---|
| WO | WO 99/38965 | 8/1999 |
| WO | WO 01/74164 | 10/2001 |

OTHER PUBLICATIONS

Charpentier et al., Journal of Cell Biology (2000) 149:503-519.
Dunn et al., J. Cell Sci. 91998) 111:3487-3496.
International Search Report mailed on Jan. 15, 2003, for PCT patent application No. PCT/EP02/02470 filed on Mar. 6, 2002, 6 pages.
Mizushima and Nagata, Nucleic Acids Research (1990) 18:5322.
Schlake et al., Proc. Natl. Acad. Sci. USA (1997) 94:3842-3847.
Schlake, Developmental Dynamics (2000) 217:368-376.
Schorp et al., Developmental Dynamics (2000) 218:537-543.

*Primary Examiner*—James S Ketter
(74) *Attorney, Agent, or Firm*—Morrison & Foerster LLP

(57) ABSTRACT

The invention relates to a method for the identification and/or production of an inhibitor of hair production. Moreover, the invention relates to a method for the inhibition of hair production. The invention also relates to a method for the production of a pharmaceutical composition. Furthermore, the invention relates to a pharmaceutical composition comprising an inhibitor of hair production identified or obtained according to one of the methods of the invention or a polynucleotide coding for the inhibitor, optionally in a pharmaceutically acceptable form of administration. The invention also relates to a pharmaceutical composition which comprises a polypeptide comprising the DNA-binding domain but not the transactivator domain of Whn, LEF-1 or Hoxc13, or a polynucleotide coding for said polypeptide, optionally in a pharmaceutically acceptable form of administration. Moreover, the invention relates to the use of a polypeptide comprising the DNA-binding domain but not the transactivator domain of Whn, LEF-1 or Hoxc13, or a polynucleotide coding for said polypeptide, of an inhibitor identified or obtained according to one of the methods of the invention or of a polynucleotide coding for such an inhibitor for the production of a pharmaceutical composition for the treatment of hair growth disorders. Not least, the invention relates to a kit for carrying out the methods of the invention.

12 Claims, 1 Drawing Sheet

Figure 1

MASSYPYDVPDYASLGGPSSPKKKRKVSRGPKPIYSYSILIFMALKNSKTGSLPVSEIYNFM
TEHFPYFKTAPDGWKNSVRHNLSLNKCFEKVENKSGSSSRKGCLWALNPSKIDKMQEELQDL
LGGSSY

IDENTIFICATION AND USE OF INHIBITORS
OF HAIR GROWTH

REFERENCE TO SEQUENCE LISTING
SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 559382000100Seqlist.txt | September 4, 2003 | 4,096 bytes |

The invention relates to a method for the identification and/or production of an inhibitor of hair production (growth). Moreover, the invention relates to a method for the inhibition of hair production. The invention also relates to a method for the production of a pharmaceutical composition. Furthermore, the invention relates to a pharmaceutical composition comprising an inhibitor of hair production identified or obtained according to one of the methods of the invention or a polynucleotide coding for the inhibitor, optionally in a pharmaceutically acceptable form of administration. The invention also relates to a pharmaceutical composition which comprises a polypeptide comprising the DNA-binding domain but not the transactivator domain of Whn, LEF-1 or Hoxc13, or a polynucleotide coding for said polypeptide, optionally in a pharmaceutically acceptable form of administration. Moreover, the invention relates to the use of a polypeptide comprising the DNA-binding domain but not the transactivator domain of Whn, LEF-1 or Hoxc13, or a polynucleotide coding for said polypeptide, of an inhibitor identified or obtained according to one of the methods of the invention or of a polynucleotide coding for such an inhibitor for the production of a pharmaceutical composition for the treatment of hair growth disorders. Not least, the invention relates to a kit for carrying out the methods of the invention.

A lot of people, in particular women, suffer from the problem of unwanted hair growth. This hair growth can be caused by disorders, e.g. as a consequence of various hormone disorders, as a consequence of the aging process or due to disposition. The most well-known form of hair removal is shaving which removes the hair on the skin surface. A further method is the electrocoagulation of the hair follicles; this method is costly and often accompanied by the irritating formation of scars. Other methods aim at a disintegration of the hair structure triggered by specific chemical substances, e.g. eflornithine as inhibitor of ornithine decarboxylase. So far, there has been no method for depilation interfering with the formation of hair per se.

Thus, the technical problem underlying the invention is to provide preparations and steps for the control of hair production, in particular for the inhibition thereof.

This technical problem is solved by the embodiments characterised in the claims. Therefore, the invention relates to a method for the identification and/or production of an inhibitor of hair production, wherein the method comprises the steps of (a) contacting a cell comprising at least one factor stimulating hair production as well as a reporter gene which is operatively linked with the expression control sequence of a target gene of the factor, with a presumed inhibitor in a medium suitable for the detection of the reporter gene;

(b) quantitative determination of the reporter gene activation in the cell;

(c) quantitative determination of the reporter gene activation in a cell as defined in (a), without the cell having been contacted with a presumed inhibitor; and (d) comparing the reporter gene activation quantitatively determined from (b) and (c), wherein a reduction or a lack of detectable reporter gene activation in (b) in comparison to (c) presents an indication for an inhibitor.

The term "inhibitor" comprises all the substances or mixtures of substances capable of inhibiting hair production. Examples of these substances or mixtures of substances are proteins, nucleic acids coding for these proteins or chemicals. Particularly important potential inhibitors of hair production are proteins, regions of proteins, protein variants or nucleic acids coding therefore, which are further described below as preferred embodiments. In the context of the invention, inhibition relates to a significant reduction of the reporter gene activation in the methods of the invention. In this context, the significance can take place by statistical methods known in the state of the art, such as e.g. the student's T-test, the $\gamma^2$-test or the U-test according to Mann-Whitney. Application criteria for the statistical methods for each individual case are known to the person skilled in the art. Moreover, adjustments of the statistical methods can be carried out by the person skilled in the art with common input. Preferably, the contacting of cells with the potential inhibitor at least leads to an inhibition of the reporter gene activation, as described in the Example and Table 1.

The term "contacting" comprises all the kinds of physical or chemical interactions between the inhibitor molecules and the cell or the cellular components. For the contacting, the inhibitor can be present in a liquid, e.g. a nutrient medium for the cell, in solution, wherein the nutrient medium is then contacted with the cell, e.g. by incubation of the cell in the medium. Instead of a liquid, gels and gel-like liquids comprising the inhibitor can be used, too. However, the term "contacting" also comprises the insertion of the inhibitor into the cell so that there the inhibitor can interact with the intracellular components like the cellular proteins. The insertion of the inhibitor can be carried out depending on its biochemical nature by various methods known in the art. In this connection, it goes without saying that the methods for the insertion of nucleic acids and the methods for the insertion of proteins or chemicals can differ. Examples of such methods suitable for the insertion of nucleic acids are precipitation transfection such as e.g. Ca-phosphate or RbCl precipitation transfection, transfection by means of liposomes, transfection by means of macromolecular polymers, e.g. fullerens, electroporation methods or transfection by retroviruses or recombination techniques for the integration into the cellular genome. Depending on the method, it might be necessary to link the nucleic acids with other nucleic acid molecules. Examples thereof are plasmids containing the nucleic acid molecules or retroviral genomes in which the nucleic acids have been integrated. After the insertion into the cell, nucleic acid molecules can also be integrated into the cellular genome.

Examples of methods for the insertion of proteins also comprise the insertion by means of liposomes, the insertion by means of macromolecular polymers such as e.g. fullerens. Some proteins, however, are actively absorbed by the cell by import. In this context, it is also possible to link proteins which would not be absorbed normally, with additional peptide sequences which are capable of mediating the import of said proteins.

Depending on their chemical or biochemical characteristics, chemicals are either imported actively by the cell and are thus inserted into the cell or they get into the cell by diffusion. Furthermore, chemicals can be inserted into the cell by means of different methods known in the state of the art. These methods comprise liposomes, macromolecular polymers.

The term "hair production" relates to the whole biological process leading to the morphological production of hair. The term further comprises different steps relevant to hair production individually. These include the formation of precursor cells of the karatinocytes and mesenchymal cells which play a role during hair production, their differentiation to mature karatinocytes, their interaction and the morphological formation of hair itself. The formation of so-called stem cells is also part of the biological process underlying the production of hair in the context of the invention. Apart from new production of hair, the term "hair production" also comprises the growth of existing hair and the underlying physiological processes thereby.

In the present invention, the term "factor" relates to proteins participating in the regulation of hair production, i.e. one or more steps of the biological process mentioned above. Proteins of this kind comprise proteins regulating the transcription, translation and/or post-translational modification of proteins or the genes coding therefore, which directly play a part in the production of hair. Proteins directly playing a part in the production of hair are proteins such as, for example, the hair keratins which are responsible for the molecular structure of the hair or the molecular phenotype of the cells participating in the production of hair. Examples of proteins regulating the transcription of the genes for proteins that play a role in the production of hair, are transcription factors which activate or enhance the gene expression of hair keratine. The term "factor" also comprises proteins capable of moldulating the activity or gene expression of the proteins acting in a regulatory manner. This includes both proteins activating or enhancing the activity of the regulatory proteins mentioned earlier and activating or enhancing their gene expression. Since regulatory proteins also includes proteins inhibiting the proteins directly playing a role in the production of hair or weakening their activity, the term "factor" also comprises proteins inhibiting or weakening the activity of regulatory proteins acting in an inhibiting manner and, thus, in the end stimulating the production of hair. Proteins acting in a regulatory manner can be divided into different classes, e.g. extracellular proteins, their cellular receptors, intracellular signal transmitters as well as proteins modifying the activity of the signal transmitters and transcription factors and their co-factors which regulate the expression of the proteins directly playing a part in the production of hair and which are regulated by the proteins mentioned earlier. In many cases, the members of these classes are connected in so-called signal transfer cascades in sequence. These signal transfer cascades particularly serve the purpose of intracellularly interpreting a signal mediated by a extracellular protein so that the cell can react to it in form of a changed gene expression. The mediation of such extracellular signals by means of signal transfer cascades consisting of proteins mentioned earlier forms the basis of intercellular communication which is of essential significance during the production of hair.

As to structure, the proteins comprised by the term "factor" have in common that they have a modular structure. This structure results from the function of these proteins which have to physically interact with either different proteins or, in the case of the transcription factors, with other proteins and the cis-regulatory DNA sequences. A modular structure means that the factors according to the invention have several domains which lie either within a single protein or within a protein built from different subunits. These domains are defined amino acid sequence segments forming a specific tertiary structure in the area of this domain. These domains can then be related to a very specific biological function such as e.g. the recognition of a specific cis-regulatory DNA element or the specific activation or inhibition of a further protein by physical interaction. According to the invention, the factors have to comprise several domains in order to be able to fulfil their biological function.

According to the invention, the factors can be inserted into the cell by means of different methods described in the art either as nucleic acids or proteins, as also described for the contacting with the inhibitors. However, according to the invention, the factors can also be present in the cell endogenously. In some cases, however, it might nevertheless be necessary to increase the concentration of the factors or the factor by exogenous addition. In any case, the factor should be present in the cell at a concentration and/or conformation which allows the activation of the reporter gene mediated by the expression control sequence.

The term "reporter gene" comprises genes which, due to their biochemical or physiochemical properties, can easily be detected directly or by means of suitable devices or methods. Particularly suitable reporter genes are described as preferred embodiments of the method of the invention in the following.

The term "expression control sequence" comprises each of the cis-regulatory elements necessary for the expression of a gene. Cis-regulatory elements are DNA sequences with regulatory properties. These include promoter, enhancer and silencer elements. Promoter elements mediate the basal expression of a gene, whereas enhancer elements achieve an enhancement of the expression, silencer elements a reduction or inhibition of the expression. The promoter, enhancer and silencer elements interact physically with regulatory proteins, the transcription factors. Transcription factors can influence the gene expression in different ways. Some transcription factors, the so-called basal transcription factors bind to DNA elements such as the TATA box or other so-called "initiator" elements, e.g. to neighbouring sequence segments. The basal transcription factors form a complex which, in the end, also recruits the RNA polymerase, a DNA-dependent enzyme which synthesises RNA and which mediates the actual transcription. Transcription factors binding to enhancer elements ensure the fast formation of a stable complex of the basal transcription factors, for example, by recruiting the basal transcription factors directly or indirectly via further proteins, the so-called co-factors, and stabilising the complex initiated in that way. Transcription factors binding to silencer elements, however, interfere with the formation of a complex of the basal transcription factors in a negative manner. A plurality of transcription factors, however, change only the structure of the DNA and, for that reason, bring closer together cis-regulatory sequences which normally have a far distance between them so that transcription factors binding thereto can interact with each other physically. It is clear that such cis-regulatory elements or the transcription factors binding thereto can also influence the gene expression as enhancer or silencer elements. On the one hand, the presence and the architecture of enhancer and silencer elements in a gene locus, on the other hand, the tissue-specific expression of the transcription factors binding to these cis-regulatory elements are responsible for the tissue-specific expression of a gene.

Within the meaning of the invention, the term "expression control sequence" relates to a DNA sequence comprising different cis-regulatory elements described earlier which suffice to mediate the expression of the reporter gene linked with this expression control sequence and which normally play a part in vivo in the mediation of the tissue specificity of the gene expression.

The term "target gene" comprises genes which are regulated by the factors of the invention in a direct or indirect manner. Factors directly regulating a target gene according to the invention are the transcription factors already mentioned earlier, whereas proteins from a regulatory signal transfer cascade, as described earlier, regulate a target gene in an indirect manner. The target genes are genes coding for proteins which either are necessary for the morphological production of hair directly or are characteristic for the molecular phenotype of a cell type essential for the production of hair.

The term "quantitative determination" relates to the determination of the whole reporter gene activation or a quantitatively significant, detectable part thereof. The determination of the reporter gene activation can take place either by quantitative detection of the transcripts of the reporter gene or by quantitative detection of the protein encoded by the reporter gene. Suitable methods for the quantitative detection of the transcripts of the reporter gene are known in the state of the art. These include, amongst others, affinity chromatography methods, mass spectroscopic methods, nucleic acid hybridisation methods, such as e.g. Northern analyses or RNase protection experiments, nuclear run-on experiments, PCR methods suitable for quantifying, such as e.g. normalised PCR, light-cycling PCR. Suitable methods for the detection of the protein encoded by the reporter gene comprise methods known in the state of the art, e.g. detection methods based on specific antibodies, like Western analyses, ELISA or RIA tests, but also methods wherein the protein is detected by the detection of its biochemical properties. Such methods can be carried out as described in the Examples. In this context, for example, enzymatic activities or chemoluminescence, bioluminescence or fluorescence can be detected. For the quantitative determination according to the invention devices are preferably used which allow the quantitative analysis of the signal produced during detection, e.g. the emission of photons with chemoluminescence or bioluminescence. Such devices and their individual application areas are known in the state of the art.

Depending on the detection method used, prior treatment of the cells can be necessary. Such treatment could, for example, serve the extraction of the reporter gene transcripts or the proteins from the cell. Such treatment methods are also known in the state of the art and described in detail, for example, in Sambrook et al., Molecular Cloning A Laboratory Manual, Cold Spring Harbor Laboratory (1989), N.Y.

For the method according to the invention to be carried out efficiently, it might be necessary that the person skilled in the art has to adjust the detection and treatment methods described in the state of the art which were referred to earlier to the conditions of the methods according to the invention. Such adjustments, however, can be carried out by the person skilled in the art relevant herein with normal efforts.

The term "comparing" means that a relative measure for the reporter gene activation is established. For this purpose, the reporter gene activation which was determined after carrying out the steps (a) and (b) mentioned above is compared to the reporter gene activation into in a cell which was not contacted with the presumed inhibitor, as described in step (c). A reduced or even missing reporter gene activation compared to the cell from step (c) which was not contacted with the inhibitor is an indication for the fact that the tested potential inhibitor is an inhibitor of hair production indeed. Within the meaning of the invention, in this context, the reduction of the reporter gene activation in an inhibitor has to be significant, as already described above. Preferably, the analysis of the reporter gene activation determined quantitatively, which comprises the comparison, can also be supported by suitable devices for electronic data processing, such as e.g. computer. Thus, a plurality of presumed inhibitors can be analysed in sequence or at the same time and the data sets obtained can be analysed effectively.

By means of the methods according to the invention, it is now possible to identify suitable agents like the inhibitors described earlier and, thus, to influence the control of the production of hair. A further advantage of the methods according to the invention is the fact that thereby depending on the choice of the target gene, specific steps of the process of the production of hair could be analysed purposefully and could be manipulated by the inhibitors found. The knowledge obtained in this way allows for the development of effective therapies of hair growth disorders and can be applied in prophylaxis and medicine on a wide scope.

A method according to the invention is preferred, wherein the reporter gene is selected from the group consisting of: $\beta$-galactosidase, luciferase, Renilla luciferase, green-fluorescent protein (GFP), blue-fluorescent protein (BFP), yellow-fluorescent protein (YFP), chloramphenicol transferase.

All the reporter genes mentioned above are very well suited for the quantitative determination by means of the activity of the proteins encoded by said reporter genes; however, it is, of course, also possible to detect the RNA transcripts. In this context, $\beta$-galactosidase, luciferase, Renilla luciferase and chloramphenicol transferase encode enzymes the activity of which can be determined efficiently by means of the substrate reacted. This quantitative determination can take place by means of methods known in the state of the art or as described in the Examples. The quantitative detection of green-fluorescent protein (GFP), blue-fluorescent protein (BFP), yellow-fluorescent protein (YFP) can be carried out based on the bioluminescent properties of these proteins.

Furthermore, a method according to the invention is preferred, wherein the target gene is selected from the group consisting of:

Keratin, human hair keratin genes: hHa1, hHa2, hHa3-I, hHa3-II, hHa4, hHa5, hHa6, hHa7, hHa8; hHb1, hHb2, hHb3, hHb4, hHb5, hHb6.

The hair keratin genes mentioned herein are particularly suitable for the methods according to the invention since they are specifically expressed during hair production and the proteins encoded by them represent essential morphological building blocks of the hair. Inhibitors capable of interfering with the gene expression of these keratins are, thus, also suitable for inhibiting the production of the essential keratin proteins. As a consequence, the morphological production of hair is inhibited efficiently. The expression control sequences mediating the tissue specificity and the efficiency of the transcription have been characterised in different hair keratin genes already so that these cis-regulatory elements are known in the state of the art and can be obtained (Schlake, Fokhead/Winged-Helix Transcription Factor Whn Regulates Hair Keratin Gene Expression: Molecular Analysis of the Nude Skin Phenotype", Developmental Dynamics 217 (2000), 368-376; Dunn et al. Regulation of a hair follicle keratin intermediate filament gene promoter. J. Cell Sci. 111, 3487-3496 (1998)). Like the relevant cis-regulatory elements of the keratin genes, transcription factors binding thereto are known in the state of the art. An example of such a regulatory transcription factor is Whn. Preferably, Whn binds to a DNA sequence comprising 10 nucleotides and the tretra-nucleotide 5'-ACGC-3'. More preferably, Whn binds to a sequence comprising the nucleotides 5'agtaagACG'cata-3' (SEQ ID NO: 1). The outstanding role this transcription factor plays for the production of hair can also be seen from the loss of its function in mice exhibiting the nude phenotype, the so-called nude mice. One characteristic of these nude mice is that they do not develop any body hair, i.e. the process of the production of hair is efficiently inhibited.

A method of the invention, wherein the reporter gene is inserted into the cell is also preferred.

The term "inserted" relates to the fact that the expression control sequence operatively linked with a reporter gene, as also discussed for the contacting above, is or was introduced into the cell as nucleic acids by different methods known in the state of the art. In this context, the reporter gene operatively linked with the expression control sequence can also be integrated into the genome of the cell stably. Moreover, the reporter gene can be linked with the endogenous expression control sequence of a target gene by means of recombination techniques. In this way, such a reporter gene would be integrated into the locus of the target gene so that the cis-regulatory elements of the target gene are still capable of regulating the gene expression, but instead of the actual target gene transcribe the reporter gene. The advantage of such a cell with stably integrated reporter gene under the control of a suitable expression control sequence would be that the step of introducing the reporter gene linked with the expression control sequence, which would otherwise be necessary when carrying out the method, could be left out. The leaving out of this step would make normalisation methods which are connected therewith and which might be necessary to guarantee the efficiency of the introduction superfluous. Nevertheless, the methods according to the invention can also be carried out by introduction of a reporter gene linked with the expression control sequence carried out individually in each process cycle. In this context, as already mentioned, it could be necessary to carry out methods for the normalisation which are suitable and which are known in the state of the art to make a meaningful comparison of two cell populations treated differently.

Furthermore, the invention relates to a method for the inhibition of hair production, wherein the method comprises the contacting of an inhibitor of hair production with a cell, wherein the cell comprises a factor stimulating the production of hair which can interact with the inhibitor.

The definitions of the terms of the methods according to the invention described above are applied mutatis mutandis to the methods described in the following.

The term "inhibition of production of hair" comprises the inhibition of individual steps of the biological process of hair production described above and the whole process. As a consequence of this inhibition, there can be a total loss of the de novo hair production or an inhibition or deceleration of the production of hair.

The term "interact" relates to the fact that the inhibitor of the factor stimulating the production of hair physically interacts therewith. As a result, the factor is inhibited in its activity and the inhibition of the production of hair is achieved.

The method according to the invention described herein can be carried out in suitable in vitro models, such as, for example, cell or organ cultures of the skin, or, however, in vivo in animal models. With methods according to the invention carried out in organ cultures of the skin or in vivo in animal models, a phenotype comparable to the phenotype of nude mice is a preferred result of the inhibition of the production of hair. The method can also be used in the therapy for hair growth disorders, as described in the embodiments regarding applications.

Preferably, the cell used in the methods according to the invention is selected from the group consisting of:

HeLa, COS-1, COS-7, CHO, epithelial cell lines, primary keratinocytes or cell lines derived from keratinocytes.

These cells or cell lines are particularly suitable for carrying out the methods of the invention, since these cells already comprise endogenous factors stimulating the production of hair or are particularly suitable for the introduction of exogenous factors, e.g. by transfection. It is known that these cells can be transfected efficiently, so that in each case a majority of the cells gets the desired characteristics.

Also, a method according to the invention is preferred, wherein the factor is encoded by a polynucleotide introduced into the cell.

The term "introduced" was described in detail above already. As described earlier, it might be necessary to introduce the factor into the cell exogenously. For this purpose, the introduction of a polynucleotide coding for the factor is particularly suitable, which, preferably, is introduced into the cell in the form of an expression construct. Apart from the polynucleotide, this expression construct comprises expression control sequences allowing the expression of the factor in the cell. According to the invention, the terms "polynucleotide" and "nucleic acid" relate to one and the same subject matters and can, therefore, be exchanged.

From the explanations given above, it also becomes clear that a method according to the invention is preferred, wherein the inhibitor is encoded by a polynucleotide introduced into the cell.

Also, a method according to the invention is preferred, wherein the factor stimulating the production of hair is a transcription factor.

From the explanations given above, it becomes clear that transcription factors stimulating the production of hair are particularly suitable for carrying out the methods according to the invention, since they directly control the expression of the genes relevant for the morphological production of hair, such as e.g. the hair keratins. Furthermore, it has already been explained that the factors according to the invention are proteins structured modularly. Transcription factors comprise at least a DNA-binding domain and a domain mediating protein interaction and, thus, have a modular structure.

In this context, a method according to the invention is particularly preferred, wherein the transcription factor is selected from the group consisting of Whn, Hairless, LEF-1 and Hoxc13. For these transcription factors it could be shown already that they play a role in the production of hair as transcription factors stimulating hair production. Moreover, the transcription factors mentioned herein exhibit a modular structure consisting of at least one DNA-binding domain and a domain mediating the interaction with further factors of the transcription complex. Furthermore, it is known for LEF-1 that, in addition, it can interact with cytoplasmic regulator proteins and/or co-factors.

The amino acid sequence for the transcription factors mentioned above is deposited with the GenBank Accession Numbers Whn: Human Y11739, Lef 1: Human AF288571, Hoxc13: Human XM006804.

Also, a method according to the invention is preferred, wherein the inhibitor comprises a domain of the transcription factor, as defined above.

A protein comprising only one domain of the transcription factor, only has the biological properties mediated by this domain. Such protein lacks properties that are mediated by the other domains of the transcription factor structured modularly and that, on the whole, are essential for its biological function. With transcription factors structured modularly, there is at least one domain mediating interactions with other proteins and one domain mediating the interaction with the cis-regulatory DNA elements. A protein comprising one domain only can, therefore, interact either with the further proteins or with the cis-regulatory element, not, however with the two. Thus, such a protein competes with the transcription factor for the interaction with either DNA or other proteins. Other proteins or cis-regulatory elements having bound the protein comprising the domain can, however, no longer interact with the transcription factor. Since the protein comprising the individual domain, however, does not have the biological activity of the whole transcription factor, the molecular interaction during gene regulation is interrupted by this protein. Thus, the described protein can act as inhibitor by competition and blocking of binding sites on either other proteins or cis-regulatory DNA elements.

From the explanations given above, it is clear that in a particularly preferred embodiment of the method according to the invention, the domain mediates a protein-DNA or protein-protein interaction.

In a preferred embodiment, a DNA-binding domain comprises the amino acids 254 to 372 of the Whn protein, whereas a domain mediating a protein-protein interaction, represents the transactivator domain of Whn comprising the amino acid 474 to 648. Further suitable deletion variants of Whn comprising one domain only are known in the state of the art and discussed by Schorpp, "Genetically Separable Determinants of Hair Keratin Gene Expression", Developmental Dynamics 218 (2000), 537-543. In this publication, suitable methods are also described which allow the person skilled in the art to determine the amino acids comprised by a DNA-binding domain or a transactivator domain. This determination of the domain can also be carried out by other methods known in the state of the art, such as e.g. by the "yeast one-hybrid" method or related methods.

Moreover, a method according to the invention is preferred, wherein the inhibitor exhibits at least an amino acid exchange, an amino acid deletion or an amino acid insertion compared to the transcription factor defined above.

Like proteins comprising only a functional domain of a transcription factor, molecular variants, too, that differ from the transcription factor by amino acid exchange, amino acid deletion or an amino acid insertion, can act as competitive inhibitors. In such molecular variants, the respective amino acid modification in one of the domains of the transcription factor structured modularly leads to the loss of the biological properties of this domain so that the molecular variant, like the protein described above, that comprises one domain of the transcription factor only, can no longer fulfil the biological function of the transcription factor; it is, however, still capable of blocking the molecular interaction during gene regulation by interaction with either other proteins or cis-regulatory DNA elements.

In the method according to the invention, the amino acid sequence of the inhibitor, however, is, despite the presence of at least one of the amino acid modifications explained earlier, at least 70%, preferably 80%, more preferably 90% or most preferably 95% identical to the amino acid sequence of the transcription factor defined above.

Therefore, a method according to the invention is particularly preferred, wherein the amino acid exchange, the amino acid deletion or the amino acid insertion leads to the loss of the function of at least one domain of the transcription factor.

Preferably, a variant Whn protein can exhibit an amino acid exchange of an arginine at position 320 in a cysteine. Such exchange would lead to the loss of the biological properties of the DNA-binding domain and, thus, to a Whn protein variant no longer capable of binding DNA, however, capable of interacting with other proteins by means of the transactivator domain. The variant of Whn mentioned above is known in the state of the art and described, for example, in Schlake (2000) loc. cit.

Furthermore, a method according to the invention is preferred, wherein the factor stimulating the production of hair is a cytoplasmic protein.

Apart from transcription factors, cytoplasmic proteins represent a further big class of regulators structured modularly. The cytoplasmic proteins according to the invention are characterised by at least two domains mediating the interaction with different further proteins. Such proteins can transfer signals, for example, by being activated themselves by a first protein via the first domain and then, in activated condition, by binding or activating a second protein via a second domain. In the end, a signal mediated by said cytoplasmic proteins regulates the gene expression of the target genes described above via transcription factors, which are at the end of the signal transfer cascade consisting of the cytoplasmic proteins. An example of such cytoplasmic proteins is the β-catenin participating in the regulation of LEF-1.

As a consequence, a method according to the invention is also preferred, wherein the inhibitor comprises a domain of the cytoplasmic protein, as defined above.

In contrast to the transcription factor, in this context, the domains mediate protein-protein interactions; each domain, however, with a different protein. Thus, in the case of the cytoplasmic proteins described herein, too, competitive inhibition is possible. Protein-binding domains can be determined by different methods known in the state of the art. These include e.g. "yeast two-hybrid" method, immune precipitation techniques and direct interaction measurements in vitro by affinity chromatography and the so-called surface plasmon resonance.

Therefore, a method according to the invention is particularly preferred, wherein the domain mediates a protein-protein interaction.

Furthermore, a method according to the invention is preferred, wherein the inhibitor exhibits at least an amino acid exchange, an amino acid deletion or an amino acid insertion compared to the cytoplasmic protein defined above.

As described for the transcription factors, the competitive inhibition can also be mediated by a molecular variant of the cytoplasmic protein, the biological function of which is impaired by the amino acid modification mentioned above.

However, in spite of the presence of at least one of the aforementioned amino acid modifications, the amino acid sequence of the inhibitor is, in the method of the invention, at least 70%, preferably 80%, more preferably 90% and most preferably 95% identical with the amino acid sequence of the cytoplasmic protein defined above.

Thus, a method of the invention is particularly preferred, wherein the amino acid exchange, the amino acid deletion or the amino acid insertion results in the loss of the function of at least one domain of the cytoplasmic protein.

Furthermore, a method of the invention is preferred, wherein the factor stimulating the production of hair is a receptor.

Receptors are also proteins with a modular structure which have at least two domains that mediate protein-protein interactions. These are, on the one hand, be the extra-cellular domain that mediates the interaction with an extra-cellular protein, the ligand, and the intracellular domain that mediates the interaction with cytoplasmic proteins. As receptors are so-called transmembrane proteins, they have an additional domain, the transmembrane domain. This transmembrane domain, however, does not mediate any protein-protein interaction but anchors the receptor to the lipid-containing plasma membrane. Like cytoplasmic proteins or transcription factors, receptors can produce or send signals and can therefore, in the end, also modulate gene expression of the aforementioned target genes by means of the signals which they sent.

Moreover, a method according to the invention is preferred wherein the inhibitor comprises a domain of the receptor as defined before.

As already described for cytoplasmic proteins, individual domains of proteins with a modular structure, such as receptors, which, by means of different domains, interact with different proteins are suitable as competitive inhibitors as they block the molecular interplay.

The protein-binding domains of the receptors can be determined with various methods described in the state of the art. These include, e.g. the yeast two-hybrid method, immunoprecipitation methods and direct interaction measurements in vitro by affinity chromatography and the so-called surface plasmon resonance.

As a consequence, a method of the invention is particularly preferred in which the domain mediates a protein-protein interaction.

In addition, a method of the invention wherein the inhibitor has at least one amino acid exchange, one amino acid deletion or one amino acid insertion compared to the receptor defined above is preferred.

As described for the transcription factors and cytoplasmic proteins, the competitive inhibition can also be mediated by a molecular variant of a receptor, the biological function of which is impaired due to the aforementioned amino acid modification. However, in the method of the invention, in spite of the presence of at least one of the explained above amino acid modifications, the amino acid sequence of the inhibitor is at least 70%, preferably 80%, more preferably 90% or most preferably 95% identical with the amino acid sequence of the receptor defined above.

In this case, a method of the invention is particularly preferred in which the amino acid exchange, the amino acid deletion or the amino acid insertion leads to the loss of the function of at least one domain of the receptor.

The invention also relates to a method for the production of a pharmaceutical composition comprising the steps of the aforementioned method according to the invention as well as the additional step of formulating the inhibitor which has been identified and/or obtained in a pharmaceutically acceptable form of administration. According to the invention, the term "pharmaceutical composition" defines substances and preparations of substances which are to heal, alleviate, prevent or recognise diseases, conditions, damage to the body or pathological discomforts by administration at or in the human body. During the method of production according to the invention, medical and/or pharmaceutical technical adjuvants can be added to the compounds identified with the methods of the invention. According to the invention, medical adjuvants are substances which are used for the production (as active ingredients) of pharmaceutical compositions in a method of the invention. Pharmaceutical technical adjuvants merely serve the suitable formulation of the pharmaceutical composition and can, if only required during the method, even be removed afterwards or form part of the pharmaceutical composition as pharmaceutically acceptable carriers. Examples of pharmaceutically acceptable carriers are listed below.

The invention furthermore relates to a pharmaceutical composition comprising, optionally in a pharmaceutically acceptable form of administration, an inhibitor of hair production which has been identified or obtained according to a method of the invention or a polynucleotide which encodes the inhibitor.

The essential terms of this embodiment have already been explained and defined above. The pharmaceutical composition is optionally formulated in combination with a pharmaceutically acceptable carrier and/or diluent.

The person skilled in the art knows examples of pharmaceutically acceptable carriers. They comprise phosphate-buffered saline, water, emulsions such as e.g. oil/water emulsions, various kinds of detergents, sterile solutions, etc. Pharmaceutical compositions comprising such carriers can be formulated with known conventional methods. These pharmaceutical compositions can be administered to an individual in a suitable dosage, e.g. in a range of 1 µg to 100 mg per day and patient. The administration can be carried out in various ways, e.g. directly on the skin, intravenously, intraperitoneally, subcutaneously, intramuscularly, locally or intradermally. Nucleic acids can also be administered in form of gene therapy. The attending doctor determines the kind of dosage depending on the clinical factors. The person skilled in the art knows that the kind of dosage depends on various factors such as e.g. the size, the surface of the body, the age, the sex or the general health of the patient, but also on the special agent that is administered, the duration and kind of the administration and on other medicaments which are possibly administered in parallel.

The invention also relates to a pharmaceutical composition comprising a polypeptide that comprises the DNA binding domain but not the transactivator domain of Whn, LEF-1 or Hoxc13 or a polynucleotide encoding said polypeptide optionally in a pharmaceutically acceptable carrier.

The invention moreover relates to the use of a polypeptide comprising the DNA binding domain but not the transactivator domain of Whn, LEF-1 or Hoxc13 or a polynucleotide encoding said polypeptide, the use of an inhibitor which has been identified and/or obtained according to a method of the invention, or of a polynucleotide encoding such an inhibitor for the production of a pharmaceutical composition for the treatment of hair growth disorders.

Symptoms of hair growth disorders are known in the state of the art and have been described in detail in medicinal standard works such as, e.g. Pschyrembel.

The further preferred or particularly preferred embodiments described for the methods of the invention apply mutatis mutandis also for the uses according to the invention.

In this case, a use according to the invention is preferred in which the hair growth disorder is increased hair growth.

Last but not least, the invention relates to a kit for carrying out the methods of the invention wherein the kit comprises a cell which comprises at least one factor stimulating the growth of hair, a reporter gene, wherein the reporter gene is operatively linked to the expression control sequence of a target gene of the factor and/or a medium that is suitable for the detection of the reporter gene.

In this case, the components of the kit according to the invention can be packaged in containers such as, e.g. vials and tubes, optionally in buffers and/or other solvents. Under certain circumstances, one or more components can be packaged in the same container.

The Figures show:

FIG. 1: The amino acid sequence (SEQ ID NO: 2) of the protein used for the competitive inhibition of the Whn transcription factor.

The Examples illustrate the invention.

EXAMPLE 1

3×105 BHK cells are transformed with the plasmid DNAs listed below using the calcium phosphate transfection method that is known in the state of the art. 24 hours after the start of the transformation, the cells are washed and fresh growth medium is added. 48 hours after the beginning of the transformation, the cells are washed, remaining medium is removed and the cells are harvested by adding TEN buffer (40 mM Tris-Cl, pH 8.0, 150 mM NaCl, 1 mM EDTA), pelleted and finally resuspended in 250 ml 250 mM Tris-Cl, pH 7.4. The cells are lysed by three times shock freezing to −80° C. and subsequent thawing at 37° C. for 3 minutes each. The lysate is then centrifuged and the supernatant is used for determining the activities of galactosidase and luciferase.

The β-galactosidase activity is determined with a method known in the state of the art using the substrate ONPG. The luciferase activity is determined with a method known in the state of the art in a luminometer by the company Berthold.

The following plasmids were used:
(a) pBOSβGal: for determining the transfection efficiency, reference: Mizushima & Nagata. pEF-BOS, a powerful mammalian expression vector. Nucleic Acids Res. 18, 5322 (1990)
(b) luc: for determining the background activity of luciferase, reference: Schlake et al. The nude gene encodes a sequence-specific DNA binding protein with homologs in organisms that lack an anticipatory immune system. Proc. Natl. Acad. Sci. USA 94, 3842-3847 (1997)
(c) luc$^{whn}$: for determining the increase of the luciferase activity triggered by the binding of the Whn transcription factor, reference: Schlake et al., loc. cit.
(d) Whn$^{wt}$: expression vector for the normal Whn protein, reference: Schlake et al., 1997
(e) Whn$^{mut}$: expression vector for the DNA binding domain of the Whn protein with a nucleic localisation signal Sequence 1 shows the amino acid sequence of the protein encoded by the expression vector Whn$^{mut}$.

Table 1 shows the results of the inhibition of the Whn-induced gene activation by a shortened Whn protein.

TABLE 1

| | plasmids | | | | luciferase activity* (average |
|---|---|---|---|---|---|
| experiment | Whnwt | Whnmut | luc | lucWhn | value +/− SD) |
| 1 | + | − | + | − | 1.0 |
| 2 | + | − | − | + | 9.65 +/− 2.3 |
| 3 | + | + | − | + | 1.07 +/− 0.65 |

*in relation to the same β galactosidase activity

---

The invention claimed is:

1. A method for the identification and/or production of an inhibitor of hair production, which method comprises the steps of:
 (a) contacting a cell comprising at least one factor stimulating hair production as well as a reporter gene which is operatively linked with the expression control sequence of a target gene of the factor, with a presumed inhibitor in a medium suitable for the detection of the reporter gene,
 wherein said factor stimulating hair production is a transcription factor selected from the group consisting of Whn, Hairless, LEF-1 and Hoxc13;
 (b) quantitative determination of the reporter gene activation in the cell;
 (c) quantitative determination of the reporter gene activation in a cell as defined in (a), without the cell having been contacted with a presumed inhibitor; and
 (d) comparing the reporter gene activation quantitatively determined from (b) and (c),
 wherein a reduction or a lack of detectable reporter gene activation in (b) in comparison to (c) presents an indication for an inhibitor.

2. The method according to claim 1, wherein the reporter gene is selected from the group consisting of β-galactosidase, luciferase, Renilla luciferase, green-fluorescent protein (GFP), blue-fluorescent protein (BFP), yellow-fluorescent protein (YFP) and chloramphenicol transferase.

3. The method according to claim 1, wherein the target gene is selected from the group consisting of Keratin, hHa1, hHa2, hHa3-1, hHa3-1I, hHa4, hHa5, hHa6, hHa7, hHa8, hHb1, hHb2, hHb3, hHb4, hHb5 and hHb6.

4. The method according to claim 1, wherein the reporter gene is introduced into the cell.

5. The method according to claim 1, wherein the cells are selected from the group consisting of HeLa COS-1, COS-7, CHO, epithelial cell lines, primary keratinocytes and cell lines derived from keratinocytes.

6. The method according to claim 1, wherein the factor is encoded by a polynucleotide introduced into the cell.

7. The method according to claim 1, wherein the inhibitor is encoded by a polynucleotide introduced into the cell.

8. The method according to claim 1, wherein the inhibitor comprises a domain of the transcription factor.

9. The method according to claim 8, wherein the domain mediates a protein-DNA or protein-protein interaction.

10. The method according to claim 8, wherein the inhibitor exhibits at least an amino acid exchange, an amino acid deletion or an amino acid insertion compared to the transcription factor.

11. The method of claim 1 which further comprises a step of formulating the inhibitor identified and/or obtained in a pharmaceutically acceptable form of administration.

12. A kit for carrying out the method according to claim 1, wherein the kit comprises a cell comprising at least one factor stimulating the production of hair, a reporter gene, wherein the reporter gene is operatively linked with the expression control sequence of a target gene of the factor, and/or a medium suitable for the detection of the reporter gene.

* * * * *

SEQUENCE LISTING

<160> NUMBER OF SEQ ID NOS: 2

<210> SEQ ID NO 1
<211> LENGTH: 14
<212> TYPE: DNA
<213> ORGANISM: Homo sapiens

<400> SEQUENCE: 1
agtaagacgc cata                                                       14

<210> SEQ ID NO 2
<211> LENGTH: 129
<212> TYPE: PRT
<213> ORGANISM: Homo sapiens

<400> SEQUENCE: 2

Met Ala Ser Ser Tyr Pro Tyr Asp Val Pro Asp Tyr Ala Ser Leu Gly
 1               5                  10                  15

Gly Pro Ser Ser Pro Lys Lys Lys Arg Lys Val Ser Arg Gly Pro Lys
                20                  25                  30

Pro Tyr Ser Tyr Ser Ile Leu Ile Phe Met Ala Leu Lys Asn Ser Lys
                35                  40                  45

Thr Gly Ser Leu Pro Val Ser Glu Ile Tyr Asn Phe Met Thr Glu His
        50                  55                  60

Phe Pro Tyr Phe Lys Thr Ala Pro Asp Gly Trp Lys Asn Ser Val Arg
 65                 70                  75                  80

His Asn Leu Ser Leu Asn Lys Cys Phe Glu Lys Val Glu Asn Lys Ser
                85                  90                  95

Gly Ser Ser Ser Arg Lys Gly Cys Leu Trp Ala Leu Asn Pro Ser Lys

-continued

```
                100                 105                 110
Ile Asp Lys Met Gln Glu Glu Leu Gln Asp Leu Leu Gly Gly Ser Ser
        115                 120                 125
Tyr
```